United States Patent
Zhang et al.

(10) Patent No.: US 12,258,570 B1
(45) Date of Patent: Mar. 25, 2025

(54) PEONY POWOX11 GENE AND APPLICATIONS OF CODED PROTEIN THEREOF

(71) Applicant: INTERNATIONAL CENTRE FOR BAMBOO AND RATTAN, Beijing (CN)

(72) Inventors: Wenbo Zhang, Beijing (CN); Zehui Jiang, Beijing (CN); Tao Hu, Beijing (CN); Yanting Chang, Beijing (CN); Yanjun Ma, Beijing (CN); Yayun Deng, Beijing (CN)

(73) Assignee: INTERNATIONAL CENTRE FOR BAMBOO AND RATTAN, Beijing (CN)

( * ) Notice: Subject to any disclaimer, the term of this patent is extended or adjusted under 35 U.S.C. 154(b) by 0 days.

(21) Appl. No.: 18/793,766

(22) Filed: Aug. 3, 2024

(30) Foreign Application Priority Data

Feb. 1, 2024 (CN) .......................... 202410140081.9

(51) Int. Cl.
*C12N 15/82* (2006.01)

(52) U.S. Cl.
CPC ....... *C12N 15/827* (2013.01); *C12N 15/8205* (2013.01)

(58) Field of Classification Search
None
See application file for complete search history.

(56) References Cited

U.S. PATENT DOCUMENTS

2022/0356481 A1*  11/2022  Sun ..................... C07K 14/415

FOREIGN PATENT DOCUMENTS

CN  114457094 A  5/2022

OTHER PUBLICATIONS

Kano-Murakami Y. et al. A rice homeotic gene, OSH1, causes unusual phenotypes in transgenic tobacco. FEBS Lett. Nov. 22, 1993; 334(3):365-8. (Year: 1993).*
Mengsi Xia, et al., A Preliminary Investigation on the Functional Validation and Interactions of PoWOX Genes in Peony (*Paeonia ostii*), Horticulturae vol. 8, No. 266, Date of issue: Mar. 20, 2022. Related pages: p. 1-22 Related claims: 1-4.
Retrieval report dated May 10, 2024 in SIPO application No. 202410140081.9.
Notification to Grant Patent Right for Invention dated May 13, 2024 in SIPO application No. 202410140081.9.

* cited by examiner

*Primary Examiner* — Cynthia E Collins
(74) *Attorney, Agent, or Firm* — Pilloff Passino & Cosenza LLP; Rachel Pilloff; Sean Passino

(57) ABSTRACT

A peony PoWOX11 gene and an application of a coded protein thereof are provided in the present disclosure, belonging to the field of biotechnology. The peony PoWOX11 gene is introduced into *Arabidopsis thaliana* to obtain a transgenic *Arabidopsis thaliana* plant stably expressing peony PoWOX11 gene, with bolting and flowering of the transgenic *Arabidopsis thaliana* plant delayed; where the peony PoWOX11 gene has a nucleotide sequence as shown in SEQ ID NO. 7, and a protein coded by the peony PoWOX11 gene has an amino acid sequence as shown in SEQ ID NO. 8.

1 Claim, 6 Drawing Sheets

Specification includes a Sequence Listing.

PEONY POWOX11 GENE AND APPLICATIONS OF CODED PROTEIN THEREOF

CROSS-REFERENCE TO RELATED APPLICATIONS

This application claims priority to Chinese Patent Application No. 202410140081.9, filed on Feb. 1, 2024, the contents of which are hereby incorporated by reference.

INCORPORATION BY REFERENCE STATEMENT

This statement, made under Rules 77 (b) (5) (ii) and any other applicable rule incorporates into the present specification of an XML file for a "Sequence Listing XML" (see Rule 831 (a)), submitted via the USPTO patent electronic filing system or on one or more read-only optical discs (see Rule 1.52 (e) (8)), identifying the names of each file, the date of creation of each file, and the size of each file in bytes as follows:
File name: US-2024-6978 Sequence
Creation date: 31 Jul. 2024
Byte size: 16,438

TECHNICAL FIELD

The present disclosure relates to the field of biotechnology, and in particular to a peony PoWOX11 gene and applications of a coded protein thereof.

BACKGROUND

The WUSCHEL-related homeobox (WOX) family is a superfamily of HB transcription factors in eukaryotic organisms, belonging to the plant-specific transcription factors, and members of the family include homeodomain (HD) that is conserved and identifiable and bindable by specific DNA sequences, and the homeodomain includes 60-66 amino acids folding into a helix-turn-helix structure. After a comprehensive study of the *Arabidopsis thaliana* genome, Haecker et al. found that the WOX gene family of *Arabidopsis thaliana* includes a total of 15 genes grouped into three subdivisions: the evolutionary branch/WUS branch (WUS and WOX1-7), the intermediate branch (WOX8-9 and WOX11-12), and the ancient branch (WOX10 and WOX13-14). In addition to HD, which is conserved among all members of the WOX family, there are four main specific motifs of WOX transcription factors in *Arabidopsis thaliana*, which are WUS-box, EAR-like motif, STF-box and MAEWEST/WOX4-box. Members of the WUS/modern branch have a specific WUS-box near the C-terminus. An EAR-like motif, including WUS and WOX5 subunits, is found at the C-terminus of WUS, WOX5 and WOX7 homologues. MAEWEST/WOX4-box is located at the N-terminus of HD and exists only in the homologues of WOX1 and WOX4, but its function is unknown. The STF-box is found only at the C-terminus of WOX1 and WOX6 homologues and has been shown to be required for STF (STENOFOLIA) inhibitory function in leaf and flower development.

The WOX gene is involved in plant embryogenesis and meristem formation, and forms the regulatory network of plant embryo development together with the cell-specific marker gene SERK (somatic embryogenesis receptor kinase), which is considered to have embryogenesis ability, the BABY BOOM (BBM) that plays a role in the promotion of cell division, the main regulator of embryogenesis, and the LEC1 that regulates the activation of other members of the Leafy Cotyledon (LEC) gene family (LEC2, FUS3, and ABI3). Members of the WOX gene family are functionally redundant, compensatory and specific, and are at the key position of the regulatory network pathway, belonging to the key node genes in the plant somatic embryo developmental regulatory network.

Studies have shown that members of the WOX family have a wide range of functions and play a role in a number of processes, including the formation of plant apical meristem, maintenance of stem cells, formation of lateral and floral organs, embryonic development, hormone signal transduction, and stress-resistant metabolism, with particularly important regulatory effects on the regions of intense cell proliferation and differentiation. In *Arabidopsis thaliana*, WOX11 and WOX12 are functionally redundant with each other, participating in adventitious root genesis and development and in vitro formation of callus, and functioning in the upstream to activate AtWOX5 and AtWOX7. Similar functions of OsWOX11 in rice crown root development by regulating cytokinin signaling have been reported in the prior art. OsWOX11 also controls root hair and root system development, thereby endowing drought resistance. The BpWOX11 gene induces genes related to expansion proteins and the cell division pathway to promote adventitious root formation in birch cuttings. In addition, the presence of the transcription factor WOX11 is required for crown root proliferation induced by overexpression of OsYUCs (OsYUC3, OsYUC4, OsYUC8, OsYUC10, OsYUC11, and OsYUC14). *Populus* WOX11/12a promotes salt tolerance in the poplar by enhancing ROS scavenging, and WOX11 in rice recruits histone H3K27me3 demethylase to promote the expression of related genes during rice shoot development. Although WOX11 has been widely studied in *Arabidopsis thaliana*, rice and *Populus trichocarpa*, the function in peony has not been reported.

Somatic embryogenesis is one of the important ways of plant regeneration in vitro, an effective way of rapid reproduction, and the focus of peony tissue culture in the future. Currently, studies on functional genes in peony mainly focus on flower and leaf color, flower type, flowering time, stress resistance, postharvest, bud dormancy, and seed dormancy, while few studies have been conducted on genes related to somatic embryogenesis in peony. WOX gene family plays a key role in the regulation network of plant somatic embryo development, and belongs to the key node genes in the regulation network of plant somatic embryo development. Therefore, it is of great significance to investigate the functional properties of embryonic genes WOX and their expression characteristics throughout the direct somatic embryogenesis and in various tissues of overexpressing *Arabidopsis thaliana*, so as to establish a complete system of plant regeneration and genetic transformation in peony.

SUMMARY

The objective of the present disclosure is to provide a peony PoWOX11 gene and applications of a coded protein thereof, so as to solve the problems existing in the prior art. The present disclosure takes *Arabidopsis thaliana* as a model plant, and provides a certain theoretical basis for establishing a complete plant regeneration and genetic transformation system for peony by exploring the expression characteristics of the PoWOX11 gene in various tissues expressing *Arabidopsis thaliana*.

In order to achieve the above objectives, the present disclosure provides the following technical schemes.

The present disclosure provides a peony PoWOX11 gene and an application of a coded protein thereof in delaying bolting and flowering of *Arabidopsis thaliana*, where the peony PoWOX11 gene has a nucleotide sequence as shown in SEQ ID NO. 7; and a protein coded by the peony PoWOX11 gene has an amino acid sequence as shown in SEQ ID NO. 8.

The present disclosure also provides a method for delaying bolting and flowering of *Arabidopsis thaliana*, including the following steps: introducing peony PoWOX11 gene into *Arabidopsis thaliana* to obtain a transgenic *Arabidopsis thaliana* plant stably expressing the peony PoWOX11 gene, and delaying bolting and flowering of the transgenic *Arabidopsis thaliana* plant; where the peony PoWOX11 gene has a nucleotide sequence as shown in SEQ ID NO. 7.

The present disclosure also provides an application of peony PoWOX11 gene and a coding protein thereof in regulating leaf morphology of *Arabidopsis thaliana*, where the peony PoWOX11 gene is overexpressed to cause curling in *Arabidopsis thaliana* leaves; and the peony PoWOX11 gene has a nucleotide sequence as shown in SEQ ID NO. 7; and a protein coded by the peony PoWOX11 gene has an amino acid sequence as shown in SEQ ID NO. 8.

Optionally, the curling includes symmetrical curling and twisting of blades along an axis of symmetry.

The present disclosure also provides a method for regulating and controlling leaf morphology of *Arabidopsis thaliana*, including following steps:

introducing peony PoWOX11 gene into the *Arabidopsis thaliana* to obtain a transgenic *Arabidopsis thaliana* plant stably expressing the peony PoWOX11 gene, causing curling of leaves of the transgenic *Arabidopsis thaliana* plant; where the peony PoWOX11 gene has a nucleotide sequence as shown in SEQ ID NO. 7.

Optionally, the curling includes symmetrical curling and twisting of blades along an axis of symmetry.

The present disclosure also provides an application of the peony PoWOX11 gene and a coded protein in regulating somatic embryogenesis of *Arabidopsis thaliana*, where the peony PoWOX11 gene is overexpressed to cause a formation of root callus of *Arabidopsis thaliana*;

a nucleotide sequence of the peony PoWOX11 gene is shown in SEQ ID NO. 7; and an amino acid sequence of a protein encoded by the peony PoWOX11 gene is shown in SEQ ID NO. 8.

The present disclosure also provides a method for regulating somatic embryogenesis of *Arabidopsis thaliana*, including following steps: overexpressing peony PoWOX11 gene in *Arabidopsis thaliana* to promote a formation of root callus of *Arabidopsis thaliana*;

a nucleotide sequence of the peony PoWOX11 gene is shown in SEQ ID NO. 7; and an amino acid sequence of a protein encoded by the peony PoWOX11 gene is shown in SEQ ID NO. 8.

The present disclosure achieves the following technical effects.

According to present disclosure, the peony PoWOX11 gene is cloned from the cultivated *Paeonia* ostii 'Fengdan', and the sequence and phylogenetic tree are analyzed to determine that it belongs to a sub-branch of ancient branch of the WOX gene family. After transforming it into *Arabidopsis thaliana*, through phenotypic comparison, it is found that peony PoWOX11 gene delays the bolting and flowering of *Arabidopsis thaliana*, and at the same time affect the leaf development, making the leaves on the axis of symmetry curl and twist symmetrically; using PoWOX11 transgenic *Arabidopsis thaliana* roots to induce callus, no fluorescence is found in normal roots, whereas strong fluorescent expression is found only at the roots surrounding the formed callus, suggesting that the PoWOX11 gene promotes the formation of root-induced callus tissues. According to the present disclosure, *Arabidopsis thaliana* is taken as a model plant, and by exploring the expression characteristics of PoWOX11 gene in various tissues of overexpressed *Arabidopsis thaliana*, a certain theoretical basis is provided for establishing a complete plant regeneration and genetic transformation system of peony.

BRIEF DESCRIPTION OF THE DRAWINGS

In order to explain the embodiments of the present disclosure or the technical scheme in the prior art more clearly, the drawings needed in the embodiments are briefly introduced below. Obviously, the drawings described below are only some embodiments of the present disclosure, and other drawings may be obtained according to these drawings without creative work for ordinary people in the field.

DETAILED DESCRIPTION OF THE EMBODIMENTS

Figure 1:
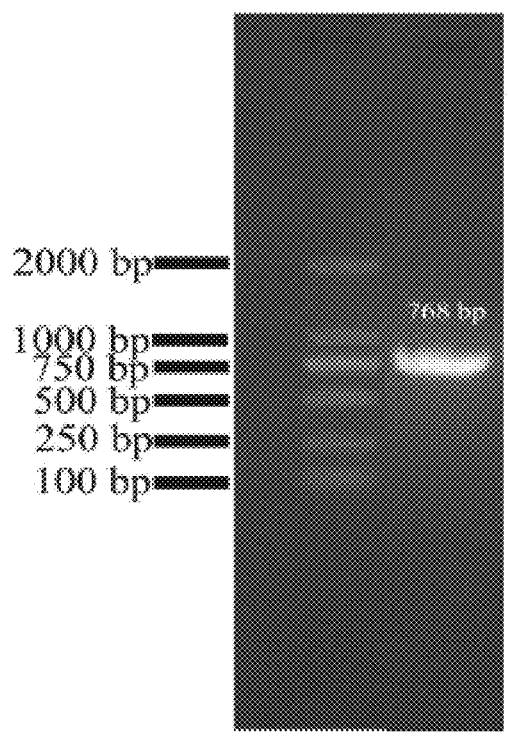
FIG. 1 is a polymerase chain reaction (PCR) electrophoresis diagram of peony PoWOX11 gene.

A number of exemplary embodiments of the present disclosure will now be described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used to limit the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges may be independently included or excluded from the range.

Unless otherwise specified, all technical and scientific terms used herein have the same meaning as commonly understood by one of ordinary skill in the art to which this present disclosure relates. Although the present disclosure only describes the preferred methods and materials, any methods and materials similar or equivalent to those described herein can also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present disclosure without departing from the scope or spirit of the present disclosure. Other embodiments will be apparent to the skilled person from the description of the present disclosure. The description and example of that present disclosure are exemplary only.

The terms "including", "comprising", "having" and "containing" used in this description are all open terms, which means including but not limited to.

Embodiments

I. Experimental Methods

1. Materials

The cultivated peony (*Paeonia* ostii, or 'Fengdan') is selected as the material, and the seeds are purchased from the peony nursery in Heze, Shandong Province of China. The round, full and glossy seeds of 'Fengdan' are selected and soaked in water at room temperature for 2-3 days, the outer skin is peeled off, then the seeds are rinsed with running water for 2 hours (h), sterilized with 75% alcohol for 30 seconds(s), washed with sterile water for 3-5 times, sterilized with 2% sodium hypochlorite solution for 20 minutes (min), washed with sterile water for 3-5 times, and the surface water is drained off, and then the seed embryos are stripped and placed in *Paeonia* ostii somatic embryo induction medium for somatic embryo induction culture, which is used for subsequent gene cloning and functional studies of its overexpression in *Arabidopsis thaliana*. The transgenic material used is Columbia wild-type (Col-0) *Arabidopsis thaliana*, which is cultured in pots in an artificial climate chamber with a light/dark cycle of 16 h/8 h, a temperature of 24±1 degrees Celsius (° C.), and a relative humidity of approximately 60 to 70%.

2. Method 2.1 Total RNA and synthesis of cDNA

Using Quick RNA Isolation Kit (Huayueyang Biotechnology (Beijing) Co., Ltd, China), the tissue culture seedlings of aseptic *Paeonia* ostii are used to extract RNA, and the concentration of RNA is determined by spectrophotometer. After the integrity of RNA bands is determined by 1% agarose gel electrophoresis, the RNA is stored in the ultra-low temperature refrigerator at −80° C. for later use. Using the extracted RNA as a template, the first strand of cDNA is synthesized by reverse transcription according to the steps of Reverse Transcription System (A3500, Promega).

2.2 Cloning of *Paeonia* ostii PoWOX11 gene

According to the principle of primer design, the primers (SEQ ID NO. 1-2 in Table 1) are designed by SnapGene (V2.3.2) software. The cDNA is used as the template, and the target sequence is amplified by the high-fidelity enzyme (TaKaRa, Kusatsu, Japan) of LA Taq kit, and detected by 1% agarose gel electrophoresis, the target sequence is obtained when the length of the target band is consistent with that of the marker sequence, and the CDS sequence of the *Paeonia* ostii PoWOX11 gene is obtained by cloning. Gel cutting is carried out on an ultraviolet gel cutting table, and the product is recovered according to the steps of DNA purification and recovery kit (Tiangen Biotech (Beijing) CO., LTD., China). The gel recovered products are connected with cloning vectors by using pMD19-T Vector Cloning Kit (TaKaRa, Kyoto, Japan), and the connection system is connected for more than half an hour for transformation. DH5a competent cells of *Escherichia coli* are transformed according to the steps of pMD19-T Vector Cloning Kit (TaKaRa, Kusatsu, Japan), then evenly coated on LB solid agar medium containing ampicillin (AMP), and monoclonal clones are selected for colony PCR after inverted culture at 37° C. for 12-16 h, positive single clones are shaken and plasmids are extracted by TIAN prep Mini Plasmid Kit (DP103-03, Tiangen Biotech (Beijing) CO., LTD., China) and 10 μL plasmid solution is sent to Anshengda (Beijing, China) for sequencing, and the correct target sequences are obtained after verification.

TABLE 1

Primer sequences

| Genes | Primer sequence F (5'-3') | Primer sequence R (5'-3') |
|---|---|---|
| PoWOX11 | ATGTGTTTTATCTTTTTC TCTCAACTCT (SEQ ID NO. 1) | AGTGGTTCTTGAAACTAG GAAATAGCTTTC (SEQ ID NO. 2) |
| Q-PoWOX11 | GCAACGCCAGATTCAAGC AAGTC (SEQ ID NO. 3) | AAGAGGAACCAGCAAGA CAAGAAGATG (SEQ ID NO. 4) |
| Q-AtActin | GGTATGGGTCAGAAAGAT GCT (SEQ ID NO. 5) | CGTTGTAGAAAGTGTGAT GCC (SEQ ID NO. 6) |

2.3 Bioinformatics Analysis

The basic physicochemical properties of *Paeonia* ostii PoWOX11 sequence are analyzed using ProtParam (ExPASy-ProtParam tool), the secondary structure of PoWOX11 protein is analyzed using SOPMA (https://npsa-prabi.ibcp.fr/cgi-bin/npsa_automat.pl?page=npsa_sopma.html), and the subcellular localization of PoWOX11 protein is predicted using Plant-mPLoc (Plant-mPLoc server (sjtu.edu.cn)).

The WOX protein sequences of *Arabidopsis thaliana, Oryza sativa, Juglans regia, Vitis vinifera, Populus trichocarpa, Amborella trichopoda, Theobroma cacao, Picea abies, Selaginella moellendorffii, Ceratopteris richardii, Ginkgo biloba* and Ostreococcus lucimarinus are obtained by homologous search from Ensembl Plants, Plant Transcription Factor Database*PlantTFDB, PlantTFDB-Plant Transcription Factor Database@CBI, PKU (gao-lab.org)) and public database NCBI (National Center for Biotechnology Information) (nih.gov), followed by Multiple sequence comparison using Clustal W; using MEGA 11 software with the neighbor-joining method and 1,000 bootstrap replicates, with other parameters as default settings, a phylogenetic tree is constructed for the obtained WOX protein sequences of all the species together with the *Paeonia ostii* PoWOX11 protein sequence. Based on the complete amino acid sequence of WOX, the WOX target gene of *Paeonia ostii* is named according to the branching result of phylogenetic tree.

The amino acid sequences of WOX4 proteins in *Arabidopsis thaliana, Oryza sativa, Juglans regia, Vitis vinifera, Populus trichocarpa* and *Paeonia ostii* are compared and analyzed by DNAMAN software. The online website WEBLOGO (http://weblogo.berkeley.edu/logo.cgi) is used to draw the sequence identification map.

2.4 Functional verification of transforming *Paeonia ostii* PoWOX11 gene into *Arabidopsis thaliana*

PoWOX11 gene is cloned into plant expression vector pBI121, and stable genetic 35S::PoWOX11 overexpressed transgenic *Arabidopsis thaliana* plants are obtained by *Agrobacterium*-mediated inflorescence infection. Overexpressed transgenic *Arabidopsis thaliana* of T3 generation and wild-type control are planted and cultured under the same culture conditions.

2.5 Fluorescence Quantitative Analysis

Tissues from root, stem, leaf, flower and fruit of *Arabidopsis thaliana* transcribed with PoWOX11 gene in T3 generation are taken and subjected to reverse transcription of the 1st strand of cDNA after extracting RNA, followed by 10-fold dilution in ddH$_2$O as a template, and the primers in Table 1 (SEQ ID NO. 3-6) are used to complete the reaction on a QTOWER real-time fluorescence quantitative PCR instrument (analytik jena, Germany) using the TB Green Premix Ex Taq II Fluorescence Quantification Kit (Tli RNaseH Plus, TaKaRa). The PCR reaction system is TB Green Premix Ex Taq 5 µL; Template 1 µL; Primer (F+R) 0.4 µL; ddH$_2$O replenished to 10 µL, a total of 3 biological replicates are set up, and the reaction conditions are pre-denaturation of 95° C. for 90 s; denaturation of 95° C. for 5 s, and unchaining of 60° C. for 30 s, 40 cycles; the dissolution curve of 60 to 95° C., with 1° C. temperature increase every 15 s. The relative expression of PoWOX11 in each part of the tissues is analyzed by using AtActin as the internal reference gene and the expression in *Arabidopsis thaliana* root tissues as the control group, and the relative expression is calculated by the $2^{-\Delta\Delta CT}$ method.

II. Results and Analysis

1. Clone and sequence analysis of *Paeonia ostii* PoWOX11 gene

The nucleotide sequence of *Paeonia ostii* PoWOX11 with the expected length is shown in FIG. 1, and the length of its CDS sequence is 768 bp. The sequencing results show that the nucleotide sequence of *Paeonia ostii* PoWOX11 gene is as shown in SEQ ID NO. 7.

```
SEQ ID NO. 7:
ATGGAAGATCATGACCCTAACAGTCCAAGGCATGGATCAGAGAGAAATG

AGCCTGTTAGATCAAGGTGGACTCCAAAGCCAGAGCAAATCTTGATACT

CGAGTCCATTTTCAATAGTGGAATGGTAAATCCTCCAAAAGATGAAACG

GTGAGGATAAGGAAGCTACTTGAGAAATTTGGTTCAGTTGGGGATGCAA

ATGTCTTCTACTGGTTTCAAAACCGGCGGTCAAGATCTCGCCGCCGGCA

ACGCCAGATTCAAGCAAGTCTTGTGGGAGAGAAGTCTACTGATCATCAT

CACCTGGCACAACAACTCACTGATGGTGGCGGTGCAATTCAATATCAAA

CTAGTTTCGCCTGTACAGGCAGCTTCTCCCCTTCTCCCACTTTCACTCT
```

```
-continued
CTCTCCATCTTCTTGTCTTGCTGGTTCCTCTTCTTCATCTGGAGTT

AATATGGGCGAAGATGGGGTTAATGATTTCTTCTCCATCTCTAATCAAA

TGGGTCTTCCGGATATGGAGCATAGCTCGGCTATAACATCAATTTTGTG

CCCTTCAGATACTTCAAATGTGCACTACCAATCTGGATTCATCACAGTG

TTCATTAATGGGGTTGCAACAGAGGTTCCAAGGGGGGCCCTTGACATGA

AAGCAATGTTTGGTCAAGATTTCGTGTTGGTTCATTCCTCTGGAATGCC

AGTCCCATTCAATGAATATGGTTTTACAATGCAAAGCTTGCAGCATGGT

GAAAGCTATTTCCTAGTTTCAAGAACCACTTAA.
```

The basic physicochemical properties of the *Paeonia ostii* PoWOX11 gene are analyzed, with an open reading frame of 765 bp, encoding 255 amino acids, a relative molecular mass of about 28.17 kDa, a theoretical isoelectric point of 6.13, an instability coefficient II of 67.96, a total average hydrophilicity of −0.46, and a lipid coefficient of 61.88, making this protein presumably an unstable hydrophilic protein. The amino acid sequence of *Paeonia ostii* PoWOX11 is shown in SEQ ID NO. 8.

```
SEQ ID NO. 8:
MEDHDPNSPRHGSERNEPVRSRWTPKPEQILILESIFNSGMVNPPKDET

VRIRKLLEKFGSVGDANVFYWFQNRRSRSRRRQRQIQASLVGEKSTDHH

HLAQQLTDGGGAIQYQTSFACTGSFSPSPTFTLSPSSCLAGSSSSSSGV

NMGEDGVNDFFSISNQMGLPDMEHSSAITSILCPSDTSNVHYQSGFITV

FINGVATEVPRGALDMKAMFGQDFVLVHSSGMPVPFNEYGFTMQSLQHG

ESYFLVSRTT.
```

Subcellular localization prediction of *Paeonia ostii* PoWOX4 protein reveals that it is localized in the nucleus. The secondary structure of *Paeonia ostii* PoWOX11 protein is analyzed by SOPMA, and it is found that the secondary structure of *Paeonia ostii* PoWOX11 protein consists of 20.11% α-helices, 15.76% β-folds, 9.24% extended strands, and 54.89% irregular coils.

2. Phylogenetic tree analysis of *Paeonia ostii* PoWOX11 protein

Figure 2:
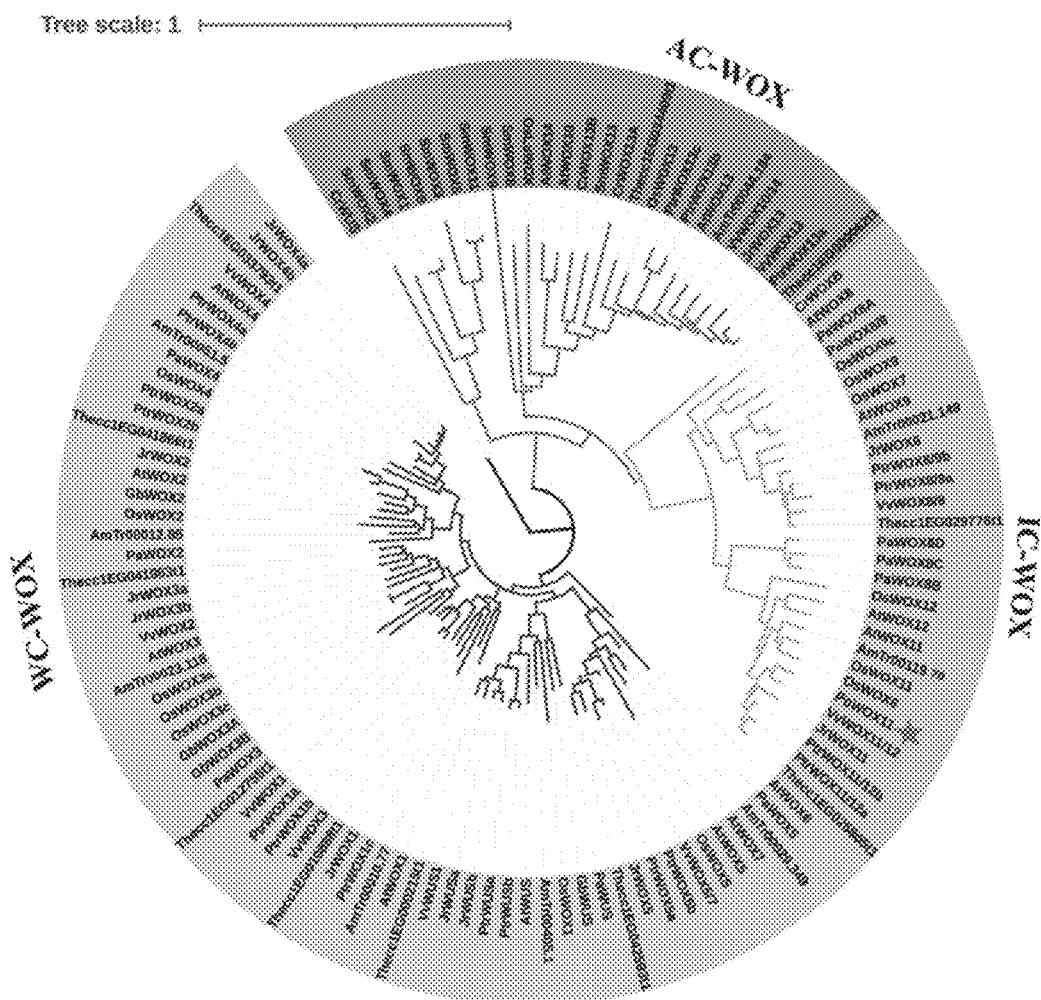
FIG. 2 shows the phylogenetic evolutionary tree of WOX genes in plants, where PoWOX11 is highlighted with a pentagram, CrWUS to Thecc1EG00006211 is AC-WOX, CrWOXB to Thecc1EG025805tlt is IC-WOX, and AtWOX6 to JrWOX4a is WC-WOX.

In order to further understand the evolutionary relationship of *Paeonia ostii* PoWOX11 gene family, PoWOX11 gene is compared with 108 sequences from 12 species and the phylogenetic tree is constructed (FIG. 2). The full-length sequence of WOX protein is analyzed by NJ method with MEGA 11. A total of 109 WOX sequences from 13 species are divided into three branches: modern branch (WC-WOX), intermediate branch (IC-WOX) and ancient branch (AC-WOX). According to the evolutionary relationship, the WOX protein of *Paeonia ostii* is identified as PoWOX11, where the PoWOX11 is in the ancient branch, which is closely related to grapes.

Figure 3:
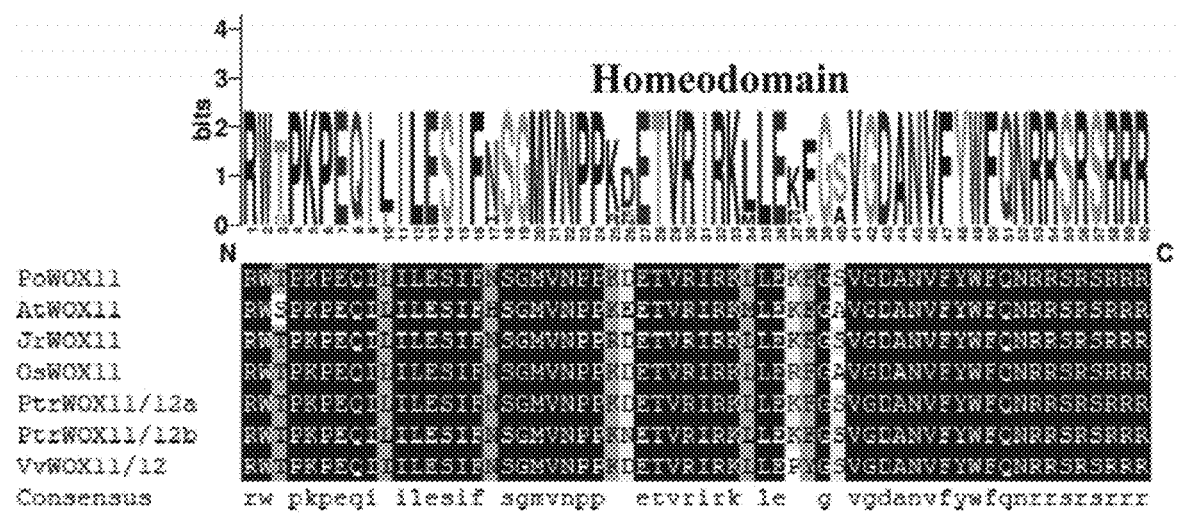
FIG. 3 shows multiple sequence comparison and sequence identity maps of WOX11 proteins in six species; where the PoWOX11 sequence is as shown in SEQ ID NO. 10, the AtWOX11 sequence is as shown in SEQ ID NO. 11, the JrWOX11 sequence is as shown in SEQ ID NO. 12, the OsWOX11 sequence is as shown in SEQ ID NO. 13, the PtrWOX1/12a sequence is as shown in SEQ ID NO. 14, PtrWOX1/12b sequence is as shown in SEQ ID NO. 15, and VvWOX11/12 sequence is as shown in SEQ ID NO. 16.

3. Multi-sequence alignment and conserved domain analysis of *Paeonia ostii* PoWOX11 protein A total of seven protein sequences of the same sub-branches of WOX11 from the model species, including *Arabidopsis thaliana, Oryza sativa* and *Juglans regia, Vitis vinifera* and *Populus trichocarpa*, are selected for multi-sequence comparison and analysis, and it is found that the peony PoWOX11 protein also contains the homologous heterodimeric structural domain HD and is highly conserved. The results of homology domain alignment show that there are many highly conserved residue sites in HD homology domain, among which the residue site of VGDANVFYWFQNRRSRSRRR (SEQ ID NO. 9) is highly conserved continuously, in which amino acid sequences indicated by dark black have 100% similarity, amino acid sequences indicated by dark grey have≥75% similarity, and amino acid sequences indicated by light grey have similarity≥50% (FIG. 3).

4. Phenotypic analysis of *Arabidopsis thaliana* overexpressing PoWOX11 gene 4.1 Phenotypes of PoWOX11 transgenic *Arabidopsis thaliana*

Figure 4:
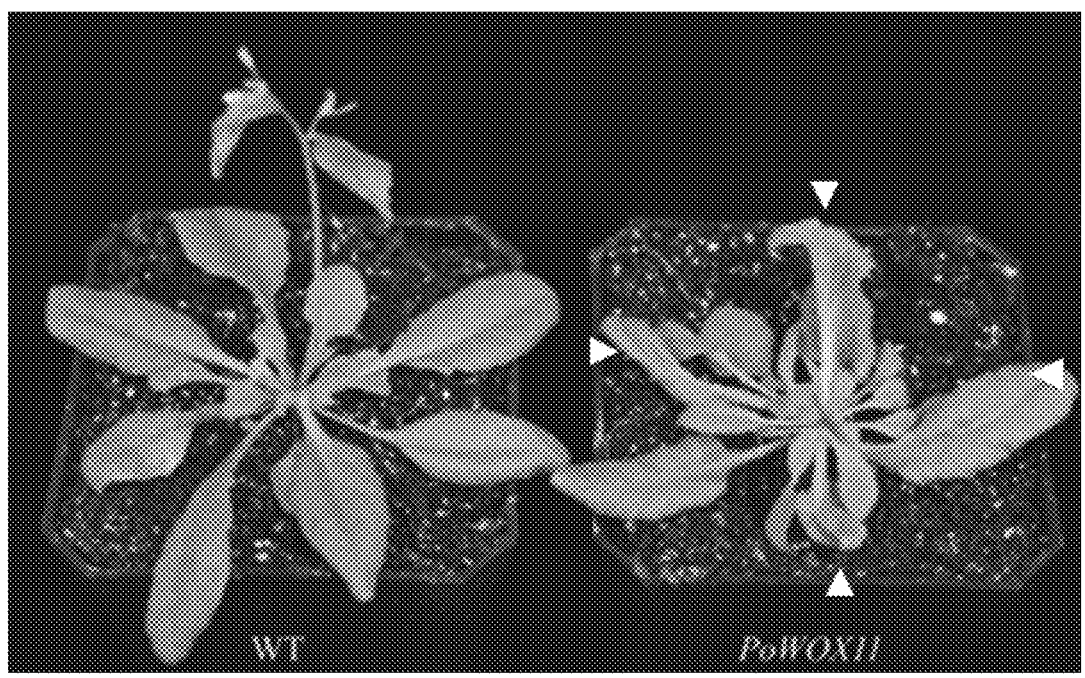
FIG. 4 shows the growth phenotypes of *Arabidopsis thaliana* overexpressed with PoWOX11, in which WT is wild type *Arabidopsis thaliana* and PoWOX11 is a transgenic overexpressed *Arabidopsis thaliana*.

Heterologous expression and phenotypic analysis of PoWOX11 are carried out on *Arabidopsis thaliana*. During the phenotypic observation of transgenic *Arabidopsis thaliana*, it is found that under the same culture conditions, the wild-type *Arabidopsis thaliana* strain has already bolted and flowered by day 28, but the PoWOX11 transgenic strain has not bolted and flowered, and the leaf blades of the PoWOX11 transgenic strain are more curled than those of the wild-type *Arabidopsis thaliana*, as shown in FIG. 4. As observed from FIG. 4, the *Arabidopsis thaliana* leaf phenotypes identified by the white triangles are the most pronounced, with leaves on the axis of symmetry showing symmetrical curling and twisting, suggesting that PoWOX11 may be associated with leaf development.

4.2 Fluorescence observation of PoWOX11 transgenic *Arabidopsis thaliana*

Figure 5A:
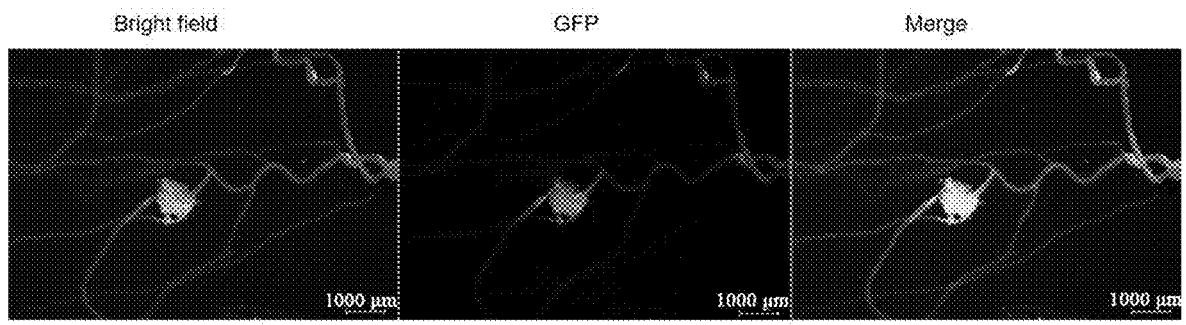
FIG. 5A is a microscopic observation of the fusion expression of PoWOX11 gene in transgenic *Arabidopsis thaliana* with a scale of 1000 micrometers (μm), including brightfield, green fluorescent protein (GFP), and brightfield and GFP merged from left to right.
Figure 5B:
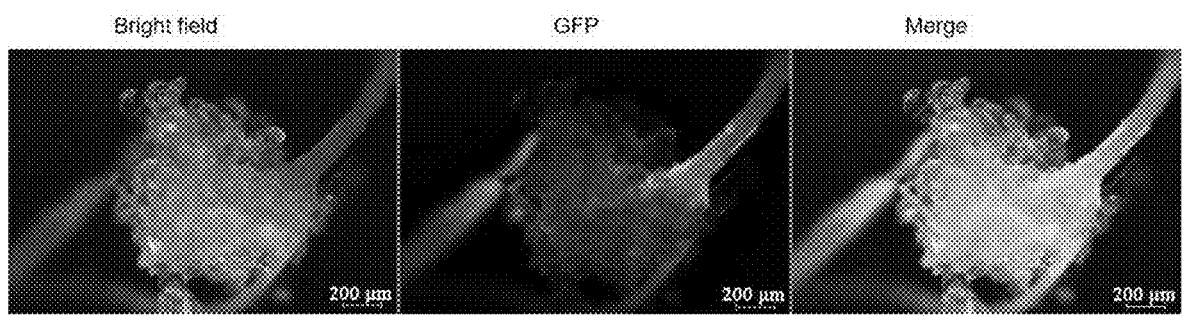
FIG. 5B is a microscopic observation of the fusion expression of PoWOX11 gene in transgenic *Arabidopsis thaliana* with a scale of 200 μm, including brightfield, GFP, and brightfield and GFP merged from left to right.

In order to understand the role of gene in callus induction, the luminescence of PoWOX11 in the callus induced by transgenic *Arabidopsis thaliana* roots is observed under the microscope. It is found that there is no fluorescence in the normal roots, but strong fluorescence expression is found only in the roots around the callus formation (FIG. 5A and FIG. 5B), indicating that PoWOX11 plays an important role in the root-induced callus formation and promotes the callus formation induced by *Arabidopsis thaliana* roots.

5. Analysis of Expression Patterns

Figure 6:
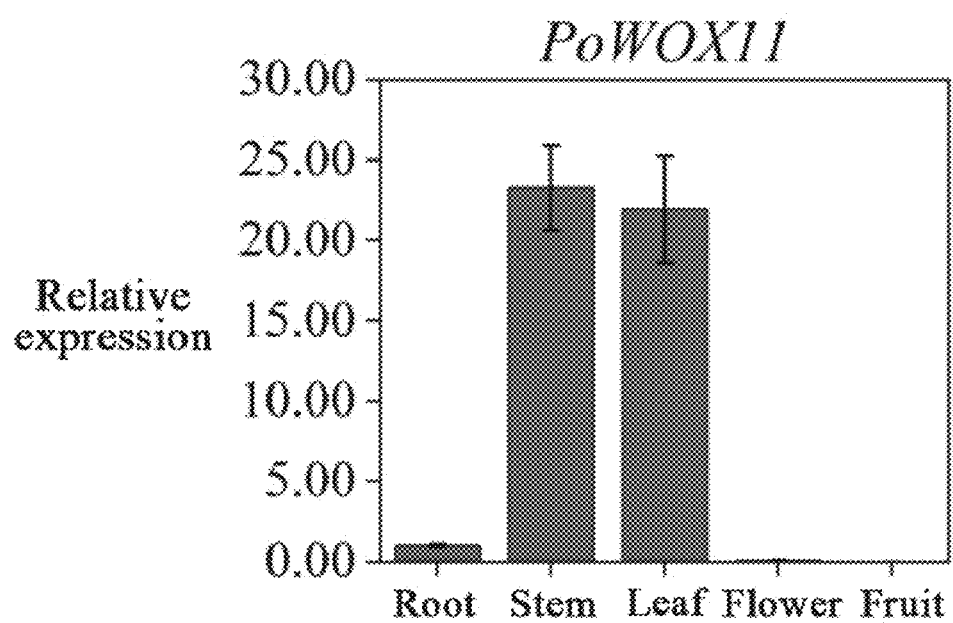
FIG. 6 shows the expressions of PoWOX11 gene in different parts of transgenic *Arabidopsis thaliana*.

RT-qPCR method is used to analyze the expression of PoWOX11 gene in *Arabidopsis thaliana* tissues (root, stem, leaf, flower and fruit) (FIG. 6). The results show that PoWOX11 is highly expressed in stems and leaves, with a certain expression in roots, a very low expression in flowers and almost no expression in fruits.

The above-mentioned embodiments only describe the preferred mode of the present disclosure, and do not limit the scope of the present disclosure. Under the premise of not departing from the design spirit of the present disclosure, various modifications and improvements made by ordinary technicians in the field to the technical scheme of the present disclosure shall fall within the protection scope determined by the claims of the present disclosure.

What is claimed is:

1. A method for delaying bolting and flowering and regulating leaf morphology of *Arabidopsis thaliana*, comprising the following steps: introducing a peony PoWOX11 gene into the *Arabidopsis thaliana* to obtain a transgenic *Arabidopsis thaliana* plant stably expressing the peony PoWOX11 gene, and delaying bolting and flowering and causing curling of the leaves of the transgenic *Arabidopsis thaliana* plant; wherein the nucleotide sequence of the peony PoWOX11 gene is SEQ ID NO.: 7; and the curling comprises a symmetrical curling and twisting of blades along an axis of symmetry.

* * * * *

SEQUENCE LISTING

```
Sequence total quantity: 16
SEQ ID NO: 1            moltype = DNA  length = 29
FEATURE                 Location/Qualifiers
source                  1..29
                        mol_type = other DNA
                        organism = synthetic construct
SEQUENCE: 1
atgtgtttta tcttttttct ctcaactct                                    29

SEQ ID NO: 2            moltype = DNA  length = 30
FEATURE                 Location/Qualifiers
source                  1..30
                        mol_type = other DNA
                        organism = synthetic construct
SEQUENCE: 2
agtggttctt gaaactagga aatagctttc                                   30

SEQ ID NO: 3            moltype = DNA  length = 23
FEATURE                 Location/Qualifiers
source                  1..23
                        mol_type = other DNA
                        organism = synthetic construct
SEQUENCE: 3
gcaacgccag attcaagcaa gtc                                          23

SEQ ID NO: 4            moltype = DNA  length = 27
FEATURE                 Location/Qualifiers
source                  1..27
                        mol_type = other DNA
                        organism = synthetic construct
SEQUENCE: 4
aagaggaacc agcaagacaa gaagatg                                      27

SEQ ID NO: 5            moltype = DNA  length = 21
FEATURE                 Location/Qualifiers
source                  1..21
                        mol_type = other DNA
                        organism = synthetic construct
SEQUENCE: 5
ggtatgggtc agaaagatgc t                                            21

SEQ ID NO: 6            moltype = DNA  length = 21
FEATURE                 Location/Qualifiers
source                  1..21
                        mol_type = other DNA
```

```
                                organism = synthetic construct
SEQUENCE: 6
cgttgtagaa agtgtgatgc c                                              21

SEQ ID NO: 7             moltype = DNA   length = 768
FEATURE                  Location/Qualifiers
source                   1..768
                         mol_type = other DNA
                         organism = synthetic construct
SEQUENCE: 7
atggaagatc atgaccctaa cagtccaagg catggatcag agagaaatga gcctgttaga    60
tcaaggtgga ctccaaagcc agagcaaatc ttgatactcg agtccatttt caatagtgga   120
atggtaaatc ctccaaaaga tgaaacggtg aggataagga agctacttga gaaatttggt   180
tcagttgggg atgcaaatgt cttctactgg tttcaaaacc ggcggtcaag atctcgccgc   240
cggcaacgcc agattcaagc aagtcttgtg ggagagaagt ctactgatca tcatcacctg   300
gcacaacaac tcactgatgg tggcggtgca attcaatatc aaactagttt cgcctgtaca   360
ggcagcttct cccttctcc cactttcact ctctctccat cttcttgtct tgctggttcc    420
tcttcttctt catctggagt taatatgggc gaagatgaag ttaatgattt cttctccatc   480
tctaatcaaa tgggtcttcc ggatatggag catagctcgg ctataacatc aatttttgtgc  540
ccttcagata cttcaaatgt gcactaccaa tctggattca tcacagtgtt cattaatggg   600
gttgcaacag aggttccaag gggggcctt gacatgaaag caatgtttgg tcaagatttc    660
gtgttggttc attcctctgg aatgccagtc ccattcaatg aatatggttt tacaatgcaa   720
agcttgcagc atggtgaaag ctatttccta gtttcaagaa ccacttaa                 768

SEQ ID NO: 8             moltype = AA   length = 255
FEATURE                  Location/Qualifiers
source                   1..255
                         mol_type = protein
                         organism = synthetic construct
SEQUENCE: 8
MEDHDPNSPR HGSERNEPVR SRWTPKPEQI LILESIFNSG MVNPPKDETV RIRKLLEKFG     60
SVGDANVFYW FQNRRSRSRR RQRQIQASLV GEKSTDHHHL AQQLTDGGGA IQYQTSFACT   120
GSFSPSPTFT LSPSSCLAGS SSSSSGVNMG EDGVNDFFSI SNQMGLPDME HSSAITSILC   180
PSDTSNVHYQ SGFITVFING VATEVPRGAL DMKAMFGQDF VLVHSSGMPV PFNEYGFTMQ   240
SLQHGESYFL VSRTT                                                   255

SEQ ID NO: 9             moltype = AA   length = 20
FEATURE                  Location/Qualifiers
source                   1..20
                         mol_type = protein
                         organism = synthetic construct
SEQUENCE: 9
VGDANVFYWF QNRRSRSRRR                                                20

SEQ ID NO: 10            moltype = AA   length = 60
FEATURE                  Location/Qualifiers
source                   1..60
                         mol_type = protein
                         organism = synthetic construct
SEQUENCE: 10
RWTPKPEQIL ILESIFNSGM VNPPKDETVR IRKLLEKFGS VGDANVFYWF QNRRSRSRRR     60

SEQ ID NO: 11            moltype = AA   length = 60
FEATURE                  Location/Qualifiers
source                   1..60
                         mol_type = protein
                         organism = synthetic construct
SEQUENCE: 11
RWSPKPEQIL ILESIFHSGM VNPPKEETVR IRKMLEKFGA VGDANVFYWF QNRRSRSRRR     60

SEQ ID NO: 12            moltype = AA   length = 60
FEATURE                  Location/Qualifiers
source                   1..60
                         mol_type = protein
                         organism = synthetic construct
SEQUENCE: 12
RWTPKPEQIL ILESIFNSGM VNPPRDETVR IRKLLEKFGS VGDANVFYWF QNRRSRSRRR     60

SEQ ID NO: 13            moltype = AA   length = 60
FEATURE                  Location/Qualifiers
source                   1..60
                         mol_type = protein
                         organism = synthetic construct
SEQUENCE: 13
RWTPKPEQIL ILESIFNSGM VNPPKDETVR IRKLLERFGA VGDANVFYWF QNRRSRSRRR     60

SEQ ID NO: 14            moltype = AA   length = 60
FEATURE                  Location/Qualifiers
source                   1..60
```

```
                        mol_type = protein
                        organism = synthetic construct
SEQUENCE: 14
RWTPKPEQIL ILESIFNSGM VNPPKDETVR IRKLLEKFGS VGDANVFYWF QNRRSRSRRR    60

SEQ ID NO: 15           moltype = AA  length = 60
FEATURE                 Location/Qualifiers
source                  1..60
                        mol_type = protein
                        organism = synthetic construct
SEQUENCE: 15
RWTPKPEQIL ILESIFNSGM VNPPKNETVR IRKLLEKFGS VGDANVFYWF QNRRSRSRRR    60

SEQ ID NO: 16           moltype = AA  length = 60
FEATURE                 Location/Qualifiers
source                  1..60
                        mol_type = protein
                        organism = synthetic construct
SEQUENCE: 16
RWTPKPEQII ILESIFNSGM VNPPKDETVR IRKLLEPYGS VGDANVFYWF QNRRSRSRRR    60
```